US006911177B2

(12) United States Patent
Deal

(10) Patent No.: US 6,911,177 B2
(45) Date of Patent: *Jun. 28, 2005

(54) ULTRAVIOLET AREA STERILIZER AND METHOD OF AREA STERILIZATION USING ULTRAVIOLET RADIATION

(76) Inventor: Jeffrey L. Deal, 1649 Savage Rd., Charleston, SC (US) 29407

( * ) Notice: Subject to any disclaimer, the term of this patent is extended or adjusted under 35 U.S.C. 154(b) by 496 days.

This patent is subject to a terminal disclaimer.

(21) Appl. No.: 10/029,787

(22) Filed: Oct. 26, 2001

(65) Prior Publication Data

US 2002/0085947 A1 Jul. 4, 2002

Related U.S. Application Data

(63) Continuation-in-part of application No. 09/665,151, filed on Sep. 19, 2000, now Pat. No. 6,656,424.

(51) Int. Cl.⁷ .......................... A61L 2/00; G01N 21/00; G01N 23/00; A62B 7/08; B01J 19/08
(52) U.S. Cl. ................. 422/24; 422/1; 422/3; 422/62; 422/121; 422/186.04; 422/300; 422/307; 250/455.11
(58) Field of Search .............................. 422/1, 3–5, 22, 422/24, 62, 119–121, 186, 186.04, 186.3, 292, 300, 305, 307, 900, 906–907; 250/455.11

(56) References Cited

U.S. PATENT DOCUMENTS 6,656,424 B1 * 12/2003 Deal ............................ 422/3

FOREIGN PATENT DOCUMENTS

| DE | 298 12 427 | 4/1999 |
| JP | 07289616 | 11/1995 |

* cited by examiner

Primary Examiner—Robert J. Warden, Sr.
Assistant Examiner—Monzer R. Chorbaji
(74) Attorney, Agent, or Firm—B. Craig Killough

(57) ABSTRACT

An ultraviolet area sterilizer (UVAS) is mobile or stationary. The UVAS is positioned in a room, such an operating room or intensive care unit. Motion detectors sense movement, to assure that personnel have evacuated the space to be sterilized. Subsequently, UV-C generators, such mercury bulbs, generate UV-C from multiple locations within the room or other enclosed space. Multiple UV-C sensors scan the room, and determine the area reflecting the lowest level of UV-C back to the sensors. The device calculates the time required to obtain a bactericidal dose of UV-C reflected back to the sensors. Once an effective bactericidal dose has been reflected to all the sensors, the unit notifies the operator and shuts down.

14 Claims, 3 Drawing Sheets

ULTRAVIOLET AREA STERILIZER AND METHOD OF AREA STERILIZATION USING ULTRAVIOLET RADIATION

This application is a continuation-in-part of application Ser. No. 09/665,151 filed Sep. 19, 2000 now U.S. Pat. No. 6,656,424.

FIELD THE INVENTION

This invention relates to methods and devices for bacterial, fungal and/or viral sterilization, and is more particularly directed to a method and device for sterilizing rooms and similar enclosed areas.

BACKGROUND OF THE INVENTION

Nosocomial, or hospital acquired, infections are common, costly, and sometimes lethal. A recent review of such infections in the cardiac surgery unit of a major hospital revealed a nosocomial infection rate of 27.3% that more than doubled the mortality rate for afflicted patients. The nature of bacteria acquired in the hospital setting differs significantly from bacteria found in a community setting primarily in their resistance to antibiotic therapy.

"Historically, *staphylococci, pseudomonads*, and *Escherichia coli* have been the nosocomial infection troika; nosocomial pneumonia, surgical wound infections, and vascular access-related bacteremia have caused the most illness and death in hospitalized patients; and intensive care units have been the epicenters of antibiotic resistance. Acquired antimicrobial resistance is the major problem, and vancomycin-resistant *Staphylococcus aureus* is the pathogen of greatest concern. The shift to outpatient care is leaving the most vulnerable patients in hospitals. Aging of our population and increasingly aggressive medical and surgical interventions, including implanted foreign bodies, organ transplantations, and xenotransplantation, create a cohort of particularly susceptible persons. Renovation of aging hospitals increases risk of airborne fungal and other infections.[1]"

[1] Nosocomial infection update.

Significant morbidity, mortality, and costs are associated with these infections. Many factors contribute to these dangerous infections. Most notably are the overuse of antibiotics and poor personal hygiene such as hand washing. Abundant evidence exists, however, that the hospital environment itself contributes to the problem by harboring virulent strains of bacteria, fungi, and viruses, and that many methods commonly used are ineffective and may actually spread contaminants.

Attempts to eradicate surface contaminates from the hospital setting have varied greatly in strategy and success. These have ranged from antiseptic soaps to fumigation with formaldehyde gas. Topical antiseptics are problematic for several reasons. First, they have recently been shown to actually induce antibiotic resistances and thus may be adding to the problem. Secondly, many surfaces such as keyboards, television sets, and monitoring controls are difficult if not impossible to decontaminate with liquid disinfectants without harming the electronics. Gas disinfection, while effective, is time consuming, hazardous to workers, and environmentally unwise.

Ultraviolet (UV) light has been long used for disinfection and sterilization. Ultraviolet light may be produced artificially by electric-arc lamps. Recently, the widespread availability of low to medium pressure mercury bulbs has led to the development of devices which use UV-C to decontaminate water supplies. UV-C is a high frequency wavelength of light within the ultraviolet band and has been shown to be the most bactericidal type of ultraviolet light. UV-C has wavelengths of about 2800 Å to 150 Å. To date, there are no published efforts to use UV-C to decontaminate or disinfect larger areas such as operating rooms. The only recent availability of the appropriate bulbs as well as significant safety concerns regarding worker exposure to UV-C likely contribute to the lack of efforts to use UV-C outside of self-contained water purification systems.

Weinstein RA Cook County Hospital, Divsion of Infectious Diseases, Chicago, Ill. 60612 Emerg Infect Dis 1998 Jul–Sep;4(3):416–20

SUMMARY OF THE INVENTION

The ultraviolet area sterilizer of the present invention (UVAS) is a mobile, automated room sterilizer. Stationary units would use the same techniques and strategy but could be built into the room itself. The UVAS is positioned in a room, such an operating room or intensive care unit, where concern exists regarding the presence of pathogenic bacteria on environmental surfaces. A wireless remote control may be used to activate the device. For an initial interval after actuation, motion detectors sense movement, to assure that personnel have evacuated the space to be sterilized. Subsequently, UV-C generators, such as a bank of mercury bulbs, generate intense levels of UV-C.

After the bulbs have reached a steady state of output, an array of UV-C sensors scan the room, and determine the darkest area, or the area reflecting the lowest level of UV-C back to the sensors. A basic stamp contained in the device calculates the time required to obtain a bactericidal dose of UV-C reflected back from darkest area. The UVAS transmits the calculated dose of UV-C, as well as other monitoring information, to the remote control where it is displayed to the user. Once a bactericidal dose has been reflected to all the sensors, the unit notifies the user and shuts down. By relying on reflected doses rather than direct exposure, the UVAS is able to sterilize or sanitize all surfaces within the room that are within view of an exposed wall or ceiling. The pathogenic bacteria in the room have been effectively eliminated.

DETAILED DESCRIPTION OF THE PREFERRED EMBODIMENT

Figure 1:
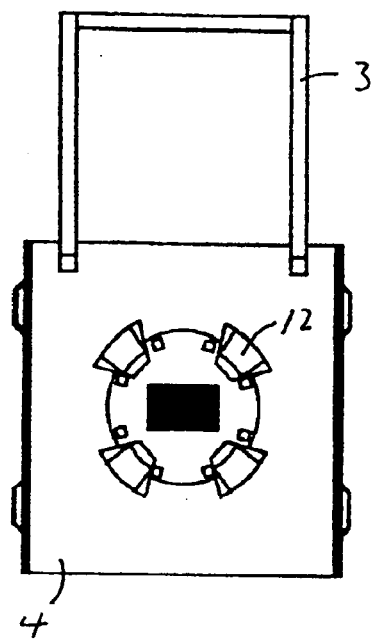
FIG. 1 is a top plan view of the device.
Figure 2:
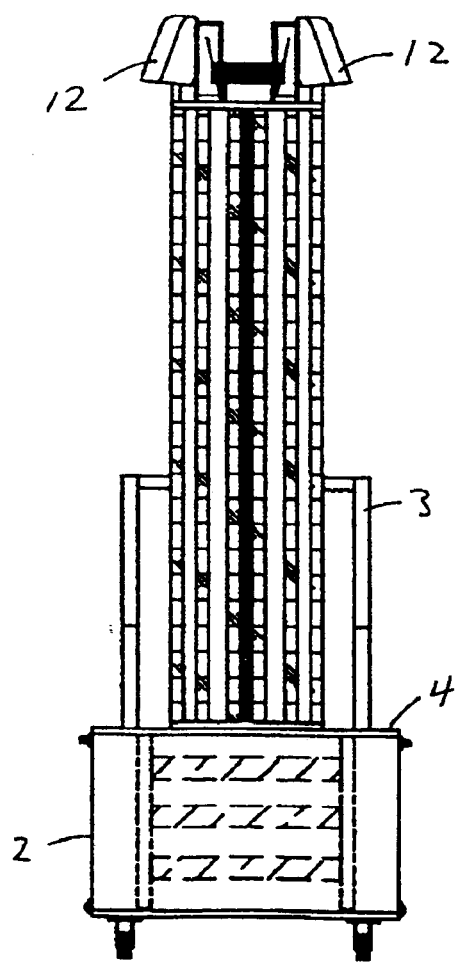
FIG. 2 is a front elevation of the device.
Figure 3:
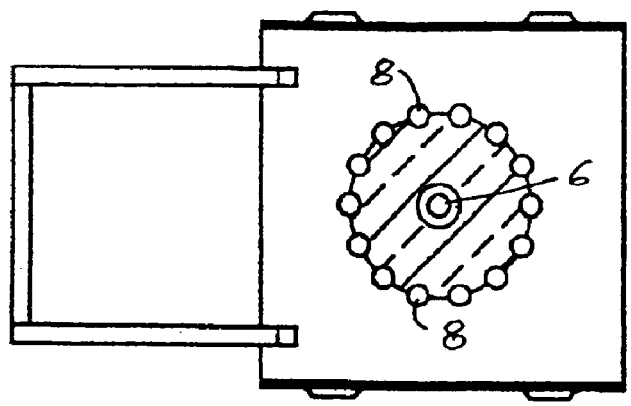
FIG. 3 is a sectioned view taken essentially along 3—3 of FIG. 4.

Referring now to the drawing figures, the UVAS is mounted on a rolling base 2 to provide portability. FIG. 2. An adjustable handle 3 is provided for transporting the device. The base includes a box 4 which could measure 30×20 cm, and in which is housed circuits, a power supply for the DC components, and the bulb ballasts. A central post rises 6 from the base to an overall height of, for example, 220 cm.

Around the central post are banks of UV-C emitting bulbs. In the embodiment as shown, six pairs of medium pressure mercury bulbs 8 are present, with each pair positioned equidistant from the pair on each side, so that they are present at 60° around the device. The bulbs may be 48-inch long, 115-Watt germicidal lamps that produce 300 microwatts of ultraviolet radiation at 1 meter. Each pair of bulbs is preferred to provide not less than 80° of coverage.

A control box on top of the unit contains wireless components, the UV-C sensor array 10, a bank of basic stamps, motion detectors 12, and audible and visible alarms. A power switch is provided on the exterior of the device. A series of plugs for control functions are also provided. A power cord is provided.

Figure 4:
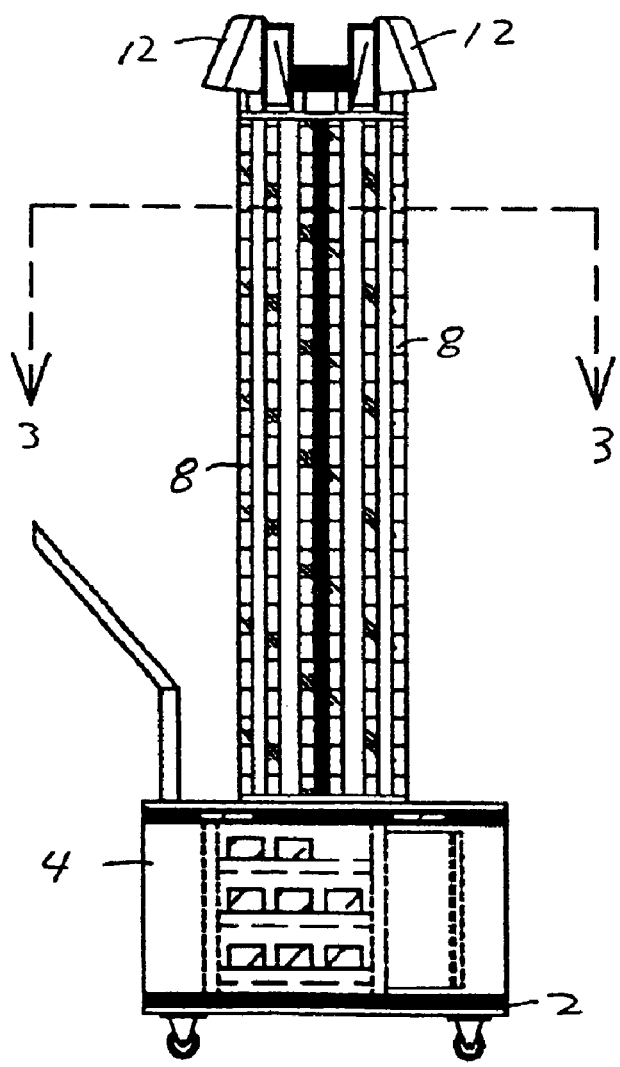
FIG. 4 is a side elevation of the device.
Figure 5:
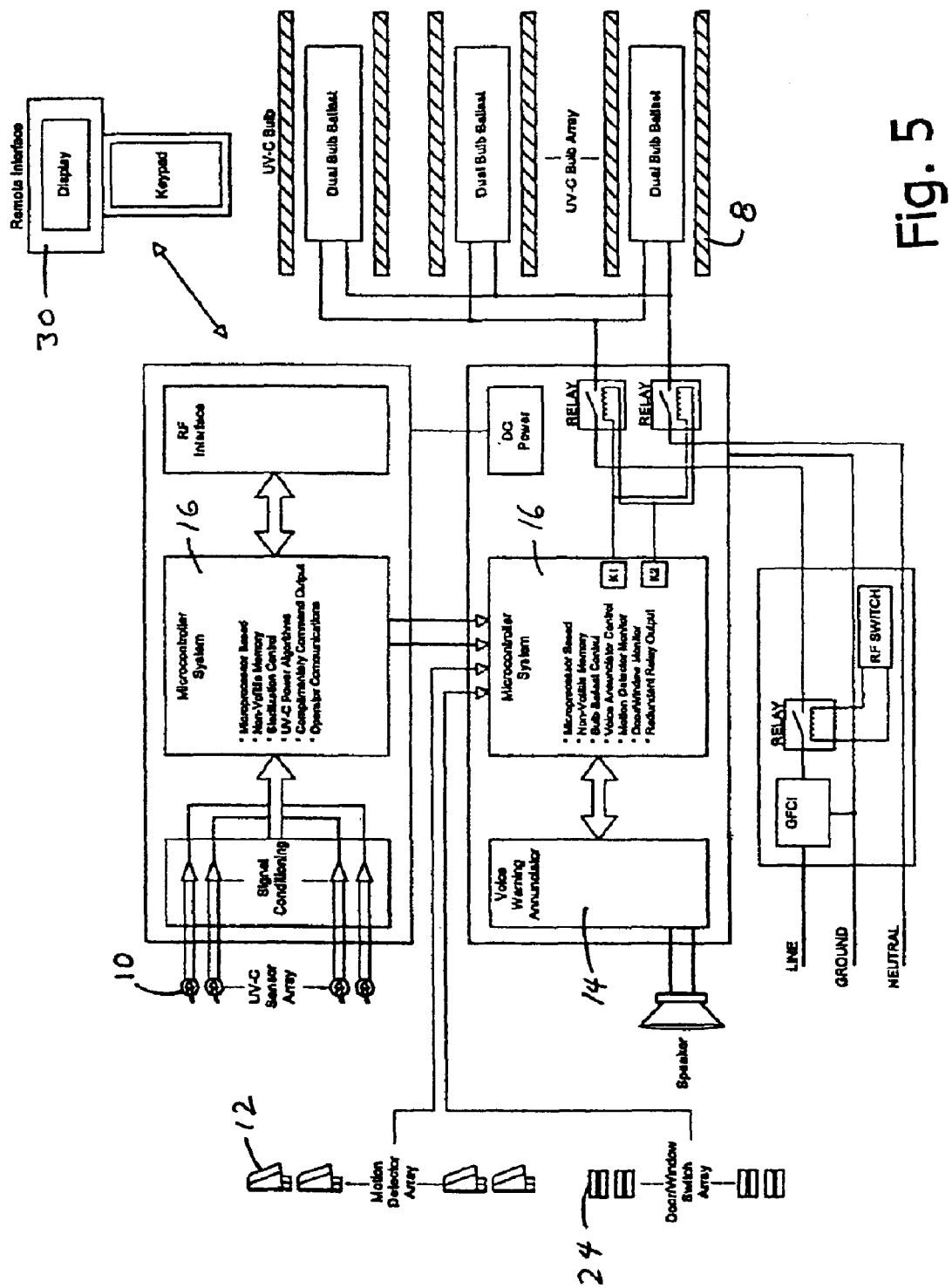
FIG. 5 is a schematic of the controls of the device.

Referring now to FIG. 4, three door contacts 24 are shown. These contacts are placed in one or more of the doors of the room in which the device is operating. The door contacts are switches which disable the device if any one of the switches is opened, such as by opening the door. The motion detectors 12 are immediately activated upon activation of the device and prior to powering of the ballasts 26 and the bulbs, by means of the time delay 28. If the motion detectors sense motion at any time during the operation of the device, power to the ballasts and the bulbs is immediately disabled. A preferred embodiment has three 120° passive ultrasonic motion detectors located on top of the device.

The UVAS is controlled by a series of programmable basic stamps which receive commands from a wireless remote control 30. A switch activates the remote control. Entry of a security code allows the user to begin sending commands to the bank of basic stamps. Commands include Activate, Shutdown, enter Sterilization Mode, or enter Sanitize Mode. The remote is in two-way communication with the UVAS and displays data from the sensor array, time left to sterilize or sanitize the room, and in case of bulb failure, the status of all numbered bank of bulbs. If two-way communication with the remote is lost, the unit shuts down.

The basic stamps activate the motion detectors at least one minute prior to activation of the UV-C bulbs and continue to monitor the detectors. They perform all calculations regarding bactericidal doses, store cumulative dosing data, and system checks to alert the user of bulb failure. This is needed since no one can actually look at the unit to check for burned out bulbs or damaged banks. The stamps can be programmed by attaching them to a personal computer via a serial port connection, thus allowing alteration to the algorithms to accommodate special circumstances.

An additional embodiment of the device provides UV-C bulbs or lamps that are placed strategically at various locations within, or directed towards, the space to be treated. The bulbs may be located at two or more locations in a room to be treated. The bulbs may be connected to the base unit, and positioned at remote locations from the base. The device in this embodiment may utilize a single bank of sensors to measure doses at locations within the area to be treated. Alternatively, multiple remote sensors, or a combination of remote and central sensors, may be provided to measure and control the dosing of UV-C to the treated area.

An example of a protocol for using the device is described.

1. A user rolls the UVAS into the room to be sterilized. After checking the room for bystanders, the user leaves with the remote control.

2. After securing the room, enters into the remote control the security code, then is prompted to presses an "on" switch on the remote control, thus activating the UVAS.

3. The audible voice alarms 14 and the motion detectors activate and stay on until the entire cycle has been complete. Should the UVAS detect motion, the unit automatically deactivates itself until the user re-enters the room and trips a breaker, thus preventing the user from re-activating the unit and harming a bystander left in the room.

4. The motion detectors stay on for a preset time, such as one minute, prior to powering the mercury bulbs and then stay active until the cycle is complete and the bulbs are powered down.

5. The bulbs are powered, and when sufficient time has elapsed to allow the bulbs to reach a steady state output (one minute or less), the basic stamp reads data from all the individual sensors located on the array. The array senses 360 degrees at a minimum with overlapping of their window of view. They are oriented away from the UVAS, thus measuring the dose of UV-C reflected back to the unit. This data is fed into the microcontroller 16 where it is integrated to compute cumulative exposure of UV-C reflected back from each sensor in the array.

6. Based on the least reflective surface or direction (of several thousand "snapshots") the microcontroller calculates the time the unit will need to stay activated to allow a bactericidal dose of UV-C to be reflected back to the unit from all directions.

7. Once sufficient time for a lethal dose of UV-C to be reflected back to the unit has elapsed, the unit powers down the bulbs and sounds an "All Clear" alert to the user.

Upon completion of the cycle, the unit has sterilized all the exposed surfaces within the room, including the primary shadows such as the back or wall side of all rails, cabinets which are not against the wall, and tables.

Trials of the UVAS in actual operating rooms and endoscopy suites and exam rooms as well as simulated trials have been performed. At direct exposure from two meters, the unit is able to reduce colony counts of common hospital pathogens by a minimum of 99.9% in one minute and achieved sterilization in 10 minutes. In one trial, the back of an exam chair was contaminated with *pseudomonas a., e. coli*, and *staphylococcus aureaus* bacteria from slurries prepared by a hospital microbiology lab. The surface was the cultured for a control prior to using the unit. It was then cultured at ten minutes and twenty minutes after activation of the unit. The test surface was not in direct line of sight of the UVAS and received only reflected doses of UV-C. Cultures using convex agar plates designed for surface cultures were used and incubated by a hospital microbiology lab. The control cultures grew greater than 100,000 colonies of all three species. The ten minute and twenty minute cultures showed no growth, demonstrating the ability of the unit to sterilize surfaces using only reflected doses. The estimated reflection from the wall in the test room was only 3%. Through the use of paint that reflects 50–85% of the UV-C, the efficiency of the device is increased, allowing for decreased exposure times.

In most environments, there is a presence of what microbiology labs label as "wild spore forms" of bacteria. These bacteria are not known to cause human disease, and yet, are resistant to low doses of UV-C. The dual programming modes of the unit allow treatment as required. One mode (Sanitize) kills all known pathogens and requires a lower exposure and thus shorter time. The other mode (Sterilize) kills all species of bacteria and requires greater cumulative doses and therefore more time.

The Ultraviolet Area Sterilizer self monitors bactericidal levels. Reflected doses of UV-C are measured, and the device remains activated until bactericidal levels are received. This ensures that areas in relative shadow and not in direct line of sight with the unit are sterilized. Also, the unit can be set to sanitize (kill common pathogens) or sterilize (kill all microbes).

Without adequate safety features, daily use of intense UV-C is dangerous and impractical. The device has motion detectors that assure the room is vacant of personnel prior to activation. Hard wired plugs on the unit are available for additional door, window, or other entry monitoring devices special situation may dictate. Once activated, the unit shuts down instantly when motion occurs anywhere in the room being sterilized. If the UVAS loses two-way communication with the remote control it also shuts down. In daily use, safety protocols commonly used in hospitals such as those in use for laser and x-ray devices may be implemented.

The UVAS is able to sanitize or sterilize all exposed surfaces in a room. It is able to do so safely, leave no residual toxins or radiation, and generates no adverse environmental side products. In addition, the UVAS is able to notify the user of the time required to perform this task and automatically shuts down upon completion of sterilization. The inventor has performed tests to prove the efficacy of the UVAS, all of which have been successful. The only limiting factor encountered to date is the reflectivity of some paints and other surfaces which absorb rather than reflect UV-C, requiring prolonged exposures of twenty minutes or greater. Highly reflective paints are beneficial to the method of area sterilization disclosed herein.

What is claimed is:

1. A method of sterilizing an area using ultraviolet radiation, comprising the steps of:
    (a) causing ultraviolet-C radiation to be emitted from multiple positions within an enclosed area;
    (b) measuring a reflection of ultraviolet-C radiation from the multiple positions within said enclosed area;
    (c) calculating an ultraviolet-C radiation reflectance level necessary to sterilize said enclosed area and comparing it with measured reflected ultraviolet-C radiation; and
    (d) terminating the emission of ultraviolet-C radiation after determining that the required ultraviolet-C radiation reflectance level has been reflected from the multiple positions within said enclosed area.

2. A method of sterilizing an area using ultraviolet radiation as described in claim 1, further comprising the step of detecting motion within said enclosed area prior to an initiation of emission of ultraviolet-C radiation.

3. A method of sterilizing an area using ultraviolet radiation as described in claim 1, further comprising the steps of detecting motion within said enclosed area prior to an initiation of emission of ultraviolet-C radiation, and disabling emission of said ultraviolet-C radiation upon detecting motion.

4. A method of sterilizing an area using ultraviolet radiation as described in claim 1, wherein reflected ultraviolet radiation is measured from at least two positions within said enclosed area that are remote from each other.

5. A method of sterilizing an area using ultraviolet radiation as described in claim 1, wherein a wall of said enclosed area reflects at least 50% of ultraviolet radiation received by said wall.

6. A method of sterilizing an area using ultraviolet radiation as described in claim 1, further comprising the step of detecting motion within said enclosed area prior to an initiation of emission of ultraviolet-C radiation.

7. A device for sterilizing an area using ultraviolet radiation, comprising:
    (a) a base;
    (b) a plurality of ultraviolet-C radiation emitters, wherein said plurality of ultraviolet-C radiation emitters are located in at least two places within an enclosed area to be treated, with each of two places remote from each other, and wherein said ultraviolet-C radiation emitters are directed towards an enclosed area to be treated; and
    (c) at least one radiation sensor which receives reflected ultraviolet-C radiation, wherein said radiation sensor measures said reflected ultraviolet-C radiation.

8. A device for sterilizing an area using ultraviolet radiation as described in claim 7, further comprising a motion detector which communicates with said plurality of ultraviolet-C radiation emitters.

9. A device for sterilizing an area using ultraviolet radiation as described in claim 7, further comprising a motion detector which communicates with said plurality of ultraviolet-C radiation emitters, wherein said motion detector prevents emission of ultraviolet-C radiation upon detecting motion within said enclosed area.

10. A device for sterilizing an area using ultraviolet radiation as described in claim 7, further comprising at least two radiation sensors that receive reflected ultraviolet-C radiation, wherein each of said at least two radiation sensors is located within the enclosed area to be treated, and at least one of said at least two radiation sensors is remote from at least one other of said at least two radiation sensors.

11. A method of sterilizing an area using ultraviolet radiation, comprising the steps of:
    (a) causing ultraviolet-C radiation to be emitted from multiple positions within an enclosed area;
    (b) measuring a cumulative reflection of ultraviolet-C radiation from each of the multiple positions within said enclosed area;
    (c) calculating an ultraviolet-C radiation reflectance level necessary to sterilize said enclosed area and comparing it with measured reflected ultraviolet-C radiation; and
    (d) terminating emission of ultraviolet-C radiation after determining that the required ultraviolet-C radiation reflectance level has been reflected from each of the multiple positions within said enclosed area.

12. A method of sterilizing an area using ultraviolet radiation as described in claim 11, further comprising the steps of detecting motion within said room prior to an initiation of emission of ultraviolet-C radiation, and disabling emission of said ultraviolet-C radiation upon detecting motion.

13. A method of sterilizing an area using ultraviolet radiation as described in claim 11, wherein reflected ultraviolet radiation is measured from at least two positions within said enclosed area that are remote from each other.

14. A method of sterilizing an area using ultraviolet radiation as described in claim 11, wherein a wall of said enclosed area reflects at least 50% of ultraviolet radiation received by said wall.

* * * * *